US012778962B2

(12) United States Patent
Sengupta et al.

(10) Patent No.: US 12,778,962 B2
(45) Date of Patent: Nov. 3, 2026

(54) USES OF RADIATION AND BENZODIAZEPINE DERIVATIVES IN CANCER THERAPIES

(71) Applicants: Emory University, Atlanta, GA (US); UWM Research Foundation, Inc., Milwaukee, WI (US)

(72) Inventors: Soma Sengupta, Atlanta, GA (US); Daniel Krummel, Atlanta, GA (US); Mohammad Khan, Atlanta, GA (US); Tahseen Nasti, Atlanta, GA (US); James Cook, Milwaukee, WI (US)

(73) Assignees: Emory University, Atlanta, GA (US); UWM Research Foundation, Inc., Milwaukee, WI (US)

( * ) Notice: Subject to any disclaimer, the term of this patent is extended or adjusted under 35 U.S.C. 154(b) by 1218 days.

(21) Appl. No.: 17/612,877

(22) PCT Filed: May 22, 2020

(86) PCT No.: PCT/US2020/034169

§ 371 (c)(1),
(2) Date: Nov. 19, 2021

(87) PCT Pub. No.: WO2020/242923

PCT Pub. Date: Dec. 3, 2020

(65) Prior Publication Data

US 2022/0079952 A1 Mar. 17, 2022

Related U.S. Application Data

(60) Provisional application No. 62/852,722, filed on May 24, 2019.

(51) Int. Cl.

| | |
|---|---|
| ***A61K 31/5513*** | (2006.01) |
| ***A61K 39/395*** | (2006.01) |
| ***A61N 5/10*** | (2006.01) |
| ***C07K 16/28*** | (2006.01) |

(52) U.S. Cl.
CPC .... *A61K 31/5513* (2013.01); *A61K 39/39541* (2013.01); *C07K 16/2818* (2013.01); *A61N 5/10* (2013.01)

(58) Field of Classification Search
None
See application file for complete search history.

(56) References Cited

U.S. PATENT DOCUMENTS

| | | | |
|---|---|---|---|
| 10,947,315 | B2 | 3/2021 | Li |
| 2010/0004226 | A1 | 1/2010 | Cook |
| 2012/0295892 | A1 | 11/2012 | Cook |
| 2015/0203483 | A1 | 7/2015 | Siegel |
| 2016/0207949 | A1 | 7/2016 | Zhao |

OTHER PUBLICATIONS

Bhattacharya, et. al., Experimental Bio and Med, 2021, 246, 2128-2135 (Year: 2021).*
Sengupta, et. al., Acta Neuropathol, 2014, 127, supplemental information (Year: 2014).*
Silk, et al., CancerMed, 2013, 2, 899-906 (Year: 2013).*
Sharabi, et al., The Lancet, 2015, 16, e498-e509 (Year: 2015).*
Begg et al. Strategies to improve radiotherapy with targeted drugs, Nat Rev Cancer, 2011, 11(4):239-53.
Brown et al. Therapeutic Targets in Radiotherapy, Int. J. Radiation Oncology Biol. Phys., vol. 49, No. 2, pp. 319-326, 2001.
Buchwald et al. Radiation, Immune Checkpoint Blockade and the Abscopal Effect: A Critical Review on Timing, Dose and Fractionation, Front Oncol, 2018, 8:612.
Calligaris et al. Distinguishing Pineoblastoma from Medulloblastomas Using Tissue Mass Spectrometry Imaging, Annals of Neurology vol. 80 (suppl 20) 2016, S228.
Cancer Genome Atlas Network, Genomic Classification of Cutaneous Melanoma, Cell. Jun. 18, 2015; 161(7): 1681-1696.
Ding et al. Newly developed strategies for improving sensitivity to radiation by targeting signal pathways in cancer therapy, Cancer Sci, 2013, 104: 1401-1410.
Dsouza et al. Combining Radiation Therapy with Immune Checkpoint Blockade for Central nervous System Malignancies Front. Oncol, 2016, 6:212.
Dunn-Pirio et al. Immunotherapy Approaches in the Treatment of Malignant Brain Tumors, Cancer 2017, 123:734-50.
Jonas et al. First in vivo testing of compounds targeting Group 3 medulloblastomas using an implantable microdevice as a new paradigm for drug development, Biomed Nanotechnol, 2016, 12(6): 1297-1302.
Kallay et al. PATH-50. Understanding the Mechanism of Benzodiazepine Mediated Cell Death in GABRA5 Overexpressing Group 3 Medulloblastomas, Neuro Oncol, 2017, 19(Suppl 6):vi182.
Kallay et al. PDTM-45. Positive Modulation of Native Gabaa Receptors in Medulloblastoma Cancer Cells With Benzodiazepines Induces Rapid Mitochondrial Fragmentation and TP53-Dependent, Cell Cycle-Independent Apoptosis, Neuro Oncol, 2018, 20(Suppl 6):vi213.
Kallay et al. Modulating native GABAA receptors in medulloblastoma with positive allosteric benzodiazepine-derivatives induces cell death, Journal of Neuro-Oncology (2019) 142:411-422.
Koblish et al. Benzodiazepinedione inhibitors of the Hdm2:p53 complex suppress human tumor cell proliferation in vitro and sensitize tumors to doxorubicin in vivo, Mol Cancer Ther, 2006, 5(1):160-9.
Krummel et al. EXTH-12. Radiation Enhances Melanoma Response to Immunotherapy and Synergizes With Benzodiazepines to Promote Anti-Tumor Activity, 2019.
Krummel et al. Impact of Sequencing Radiation Therapy and Immune Checkpoint Inhibitors in the Treatment of Melanoma Brain Metastases, Int J Radiation Oncol Biol Phys, vol. 108, No. 1, pp. 157-163, 2020.

(Continued)

*Primary Examiner* — Misook Yu
*Assistant Examiner* — Samantha Lake Hopkins
(74) *Attorney, Agent, or Firm* — Emory Patent Group

(57) ABSTRACT

This disclosure relates to uses of radiation and benzodiazepines optionally in combination with other anticancer agents for treating cancer. In certain embodiments, this disclosure relates to methods of using radiation, benzodiazepines, and check point inhibitors in cancer therapies.

6 Claims, 6 Drawing Sheets

(56) References Cited

OTHER PUBLICATIONS

Lewter et al. Antinociceptive effects of a novel α2/α3 subtype selective GABAA receptor positive allosteric modulator, ACS Chem Neurosci, 2017, 8(6): 1305-1312.
Li et al. Synthesis of chiral GABAA receptor subtype selective ligands as potential agents to treat schizophrenia as well as depression, Arkivoc 2018, part iv, 158-182.
Maaser et al. Overexpression of the Peripheral Benzodiazepine Receptor Is a Relevant Prognostic Factor in Stage III Colorectal Cancer, Clinical Cancer Research, vol. 8, 3205-3209, 2002.
Patel et al. Two heads better than one? Ipilimumab immunotherapy and radiation therapy for melanoma brain metastases, Neuro-Oncology, 17(10), 1312-1321, 2015.
Poe et al. Synthesis and Characterization of a Novel γ-Aminobutyric Acid Type A (GABAA) Receptor Ligand That Combines Outstanding Metabolic Stability, Pharmacokinetics, and Anxiolytic Efficacy, J. Med. Chem, 2016, 59, 10800-10806.
Pubchem CID: 9838431, 7-ethynyl-1-methyl-5-phenyl-3H-1,4-benzodiazepin-2-one, downloaded 2020, available at https://pubchem.ncbi.nlm.nih.gov/compound/9838431.
Sengupta et al. α5-GABAA receptors negatively regulate MYC-amplified medulloblastoma growth, Acta Neuropathol, 2014, 127(4): 593-603.
Strowd et al. Meeting update—Society for Neuro-Oncology, 2016 annual meeting, Neuro-Oncology, 19(2), 150-152, 2017.
Witkin et al. Bioisosteres of ethyl 8-ethynyl-6-(pyridin-2-yl)-4H-benzo[f]imidazo[1,5-a][1,4]diazepine-3-carboxylate (HZ-166) as novel alpha 2,3 selective potentiators of GABAA receptors: Improved bioavailability enhances anticonvulsant efficacy, Neuropharmacology, 137 (2018) 332-343.
Zhang et al Enhancement of Radiation Sensitivity of Human Squamous Carcinoma Cells by Histone Deacetylase Inhibitors, Radiation Research, 161, 667-674 (2004).

* cited by examiner

USES OF RADIATION AND BENZODIAZEPINE DERIVATIVES IN CANCER THERAPIES

CROSS-REFERENCE TO RELATED APPLICATIONS

This application is the National Stage of International Application No. PCT/US2020/034169 filed May 22, 2020, which claims the benefit of U.S. Provisional Application No. 62/852,722 filed May 24, 2019. The entirety of each of these applications is hereby incorporated by reference for all purposes.

BACKGROUND

Brain metastases is cancer from other areas of the body that spreads to the brain. Brain metastases from lung, breast, colon, kidney and skin (melanoma) are common in adult cancer patients and are associated with significant morbidity and mortality. For example, around 50% of melanoma brain metastases (MBM) have serine/threonine-protein kinase B-raf (BRAF) mutations, most commonly V600E (80%) or V600K (14%). While the first generation of a clinically active RAF-inhibitor (vemurafenib) produced high systemic objective response rates, intracranial responses were limited. Combination therapies with RAF/MEK-inhibitors, such as dabrafenib and trametinib, improved both systemic progression-free survival and intracranial responses. However, many patients acquire resistance to these therapies. Thus, there is a need to identify improvements.

Tawbi et al. report using nivolumab and ipilimumab in melanoma metastatic to the brain. N Engl J Med, 2018, 379, 722-730.

Postow et al. report immune-related adverse events associated with immune checkpoint blockade. N Engl J Med, 2018, 378, 158-168.

Begg et al. report strategies to improve radiotherapy with targeted drugs. Nat Rev Cancer, 2011, 11 (4): 239-53.

Kallay et al. report modulating native gamma-aminobutyric acid type A (GABAA) receptors in medulloblastoma with positive allosteric benzodiazepine-derivatives induces cell death. Journal of Neuro-Oncology, 2019, 142:411-422.

Sengupta et al. report alpha5-GABAA receptors negatively regulate MYC-amplified medulloblastoma growth. Acta Neuropathol, 2014, 127 (4): 593-603.

References cited herein are not an admission of prior art.

SUMMARY

This disclosure relates to uses of radiation and benzodiazepines optionally in combination with other anticancer agents for treating cancer. In certain embodiments, this disclosure relates to methods of using radiation, benzodiazepines, and check point inhibitors in cancer therapies.

In certain embodiments, this disclosure relates to methods of treating cancer comprising the steps of: administering a benzodiazepine derivative or salt thereof to a subject diagnosed with a cancer or tumor directing radiation to the cancer or tumor in combination with administering to the subject an effective amount of an anticancer agent or combination of anticancer agents.

In certain embodiments, this disclosure relates to methods of treating cancer comprising the steps of: administering a benzodiazepine derivative or salt thereof to a subject diagnosed with a cancer or tumor directing radiation to the cancer or tumor in combination with administering to the subject an effective amount of a check point inhibitor.

In certain embodiments, this disclosure relates to methods of treating cancer comprising the steps of: administering a benzodiazepine derivative or salt thereof to a subject diagnosed with a cancer or tumor; and concurrently or soon thereafter directing radiation to the cancer or tumor; and thereafter administering to the subject an effective amount of an anticancer agent or combination of anticancer agents.

In certain embodiments, the cancer is a brain cancer or tumor such as brain metastasis, melanoma brain metastasis, lung brain metastasis, breast brain metastasis, colon brain metastasis, kidney brain metastasis, acoustic neuroma, astrocytoma, choroid plexus carcinoma, craniopharyngioma, embryonal tumor, ependymoma, glioblastoma, glioma, medulloblastoma, meningioma, oligodendroglioma, or pituitary tumors.

In certain embodiments, this disclosure relates to methods of treating cancer comprising the steps of: administering a benzodiazepine derivative or salt thereof to a subject diagnosed with a cancer tumor; and concurrently or soon thereafter directing radiation to the cancer or tumor; and thereafter administering to the subject an effective amount of a check point inhibitor. In certain embodiments, the cancer is a brain cancer, brain metastasis, or melanoma brain metastasis.

In certain embodiments, this disclosure relates to methods of treating brain cancer comprising the steps of: administering a benzodiazepine derivative or salt thereof to a subject diagnosed with a brain tumor; and concurrently or soon thereafter directing radiation to the brain tumor; and thereafter administering to the subject an effective amount of a check point inhibitor.

In certain embodiments, the subject is diagnosed with a tumor, a brain tumor, brain metastasis, or melanoma brain metastasis.

In certain embodiments, the checkpoint inhibitor is an anti-CTLA-4 antibody, anti-PD-1 antibody, anti-PD-L1 antibody, or combinations thereof.

In certain embodiments, the checkpoint inhibitor is ipilimumab, nivolumab, pembrolizumab, cemiplimab, atezolizumab, durvalumab, avelumab, or combinations thereof.

In certain embodiments, the checkpoint inhibitor is a combination of nivolumab and ipilimumab.

In certain embodiments, this disclosure contemplates a compound disclosed herein for use in the production of a medicament for use in treating cancer with radiation optionally in combination with another anticancer agent, such as a check point inhibitor.

In certain embodiments, this disclosure relates to methods of treating cancer, a tumor, brain tumor, brain metastasis, or melanoma brain metastasis comprising the steps of: administering a 7-ethynyl-1-methyl-5-phenyl-1,3-dihydro-2H-benzo[e][1,4]diazepin-2-one (QH-II-066) or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

BRIEF DESCRIPTION OF THE SEVERAL VIEWS OF THE DRAWINGS

FIG. 1A shows a schematic of the tumor, anti-PD-L1, and radiation strategy. Mice were implanted in left (L) and right (R) flanks with B16F10-GP tumor cells. Mice then received either: (i) no treatment; (ii) anti-PD-L1 alone; (iii) 10 Gy administered (right flank only) on Day 10 (in the morning) before anti-PD-L1 (RT-ICI) (in the evening); (iv) anti-PD-L1 administered first, followed by 10 Gy administered (right flank only) on Day 20 (ICI-RT). Sequence of anti-PD-L1 and radiation is shown.

FIG. 1B shows data on Mean tumor volumes of right and left tumors after different treatments.

FIG. 3A shows data on the effect of dose response of QH-II-066 on tumor growth. Mice were injected daily for a week at 10, 25 or 50 mg/kg QH-II-066.

FIG. 3B is a schematic illustration of the tumor, benzodiazepine, and radiation strategy. Mice were implanted in left (L) and right (R) flanks with B16F10-GP tumor cells. Mice received either: (i) no treatment; (ii) radiation alone (10 or 5 Gy, right flank only); (iii) QH-II-066 alone at 10 mg/kg; (iv) radiation (10 or 5 Gy, right flank only) on Day 10 (in the morning), followed by QH-II-066 (10 mg/kg, in the evening). In groups that received radiation and drug, QH-II-066 (10 mg/kg) was injected daily for 7 days after radiation.

FIG. 3C shows data on the effect of combination of QH-II-066 (10 mg/kg) and 10 Gy radiation on tumor growth kinetics.

FIG. 3D shows data on the effect of combination of QH-II-066 (10 mg/kg) and 5 Gy radiation on tumor growth kinetics.

FIG. 4A shows data where mice were treated with 10 Gy radiation and 10 mg/Kg QH-II-066. Mice were sacrificed and tumor infiltrating lymphocytes (TILs) were isolated, stained, and analyzed using flow cytometry. For cytokine analysis, TILs were stimulated with GP33 peptide for 6 hours in presence of GolgiStop™ and GolgiPlug™ and analyzed using flow cytometry. Tumor weight and Lymphocyte number per gram tumor.

FIG. 4B shows data on the percent CD8 of total lymphocytes and number of CD8 T cells per gram of tumor.

FIG. 4C shows data on the percent GP33+ T cells of CD8+ T cell and number of GP33+ CD8+ T cells per gram of tumor.

FIG. 4D shows data on the percent IFN-γ+ of CD8+ T cells and number of IFN-γ+CD8+ T cells per gram of tumor.

FIG. 4E shows data on the percent IFN-γ+ TNF-α+ T cells of CD8+ T cells and number of IFN-γ+ TNF-α+CD8+ T cells per gram of tumor.

DETAILED DESCRIPTION

Figure 1A:
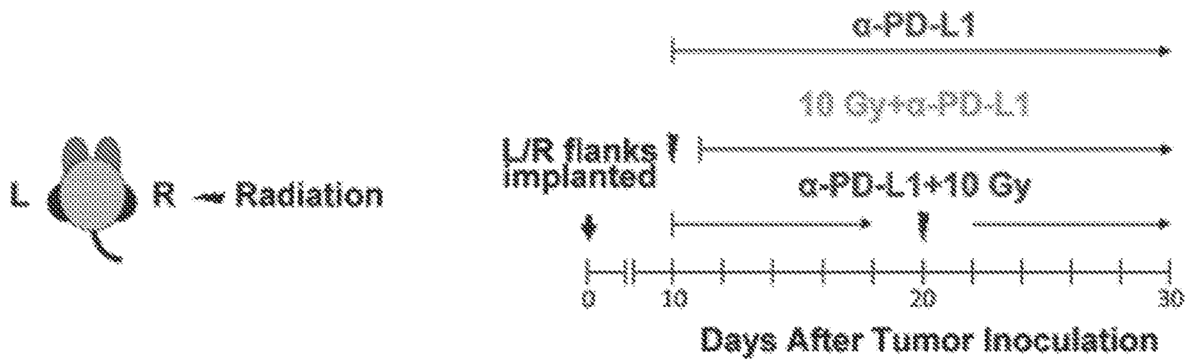
FIG. 1A-1B illustrates and shows data on sequential administration of radiation and anti-PD-L1 response in vivo.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

"Cancer" refers any of various cellular diseases with malignant neoplasms characterized by the proliferation of cells. Cancer may or may not be present as a tumor mass with a defined boundary. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof. As used herein, the term "intermixed with" when used to describe administration in combination with an additional treatment means that the agent may be administered "together with."

The term "effective amount" refers to that amount of a compound or pharmaceutical composition described herein that is sufficient to effect the intended application including, but not limited to, disease treatment, as illustrated below. In relation to a combination therapy, an "effective amount" indicates the combination of agent results in synergistic or additive effect when compared to the agents individually. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

A "chemotherapy agent," "chemotherapeutic," "anti-cancer agent," or the like, refer to molecules that are recognized to aid in the treatment of a cancer. Contemplated examples include the following molecules or derivatives such as abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

Methods

In certain embodiments, this disclosure relates to methods of treating cancer comprising the steps of: administering a benzodiazepine derivative or salt thereof to a subject diagnosed with a cancer or tumor directing radiation to the cancer or tumor in combination with administering to the subject an effective amount of an anticancer agent or combination of anticancer agents.

In certain embodiments, this disclosure relates to methods of treating cancer comprising the steps of: administering a benzodiazepine derivative or salt thereof to a subject diagnosed with a cancer or tumor directing radiation to the cancer or tumor in combination with administering to the subject an effective amount of a check point inhibitor.

In certain embodiments, this disclosure relates to methods of treating cancer comprising the steps of: administering a benzodiazepine derivative or salt thereof to a subject diagnosed with a cancer or tumor; and concurrently or soon thereafter directing radiation to the cancer or the tumor; and thereafter administering to the subject an effective amount of an anticancer agent or combination of anticancer agents. In certain embodiments, the cancer is a brain cancer such as brain metastasis or melanoma brain metastasis.

With regard directing radiation "concurrently or soon thereafter," refers to applying the radiation while the benzodiazepine derivative is present in or around the location of the cancer or tumor, e.g., due to oral, local, or systemic administration. There may be a time between administering a benzodiazepine and providing radiation, e.g., within a time period that is less than the half-life of the benzodiazepine. In certain embodiments, it is contemplated that the radiation is directed to the area/location of the cancer or tumor within one hour, within two hours, within three hours, within four hours, within eight hours, within 24 hours, or within two days of administering the benzodiazepine derivative.

In certain embodiments, radiation therapy treatment is daily. Typically, daily radiation therapy refers to for several days, e.g., 3, 4, 5 days of a week. In certain embodiments, radiation therapy treatment is for 1 to 6 weeks. In certain embodiments, radiation therapy treatment is for 2 to 6 weeks. In certain embodiments, radiation therapy treatment is for 3 to 6 weeks. In certain embodiments, radiation therapy treatment is 5 days a week for 4 to 6 weeks With regard to administering a chemotherapy agent "thereafter," the administration may be within one week, within two weeks, within three weeks, or within a month after the radiation treatment stopped. With regard to administering a chemotherapy agent "thereafter," the administration may be after one day, two days, three days, four days, five days, or after one week, two weeks, three weeks, or after a month once the radiation treatment is stopped.

In certain embodiments, this disclosure relates to methods of treating cancer comprising the steps of: administering a benzodiazepine derivative or salt thereof to a subject diagnosed with a cancer or tumor; and concurrently or soon thereafter directing radiation to the cancer or tumor; and thereafter administering to the subject an effective amount of a check point inhibitor, BRAF inhibitor, or MEK inhibitor, or combinations thereof. In certain embodiments, the cancer is a brain cancer, brain metastasis, or melanoma brain metastasis.

In certain embodiments, the anticancer agent or combination of anticancer agents is dabrafenib and trametinib. In certain embodiments, the subject is diagnosed with a BRAF V600E or V600K mutation.

In certain embodiments, this disclosure relates to methods of treating brain cancer comprising the steps of: administering a benzodiazepine derivative or salt thereof to a subject diagnosed with a brain cancer or tumor; and concurrently or soon thereafter directing radiation to the brain cancer or tumor; and thereafter administering to the subject an effective amount of a check point inhibitor.

In certain embodiments, the subject is diagnosed with cancer, a tumor, a brain tumor, brain metastasis, or melanoma brain metastasis.

In certain embodiments, the checkpoint inhibitor is an anti-CTLA-4 antibody, anti-PD-1 antibody, anti-PD-L1 antibody, or combinations thereof.

In certain embodiments, the checkpoint inhibitor is ipilimumab, nivolumab, pembrolizumab, cemiplimab, atezolizumab, durvalumab, avelumab, or combinations thereof.

In certain embodiments, the checkpoint inhibitor is a combination of nivolumab and ipilimumab.

In certain embodiments, this disclosure contemplates a benzodiazepine derivative disclosed herein for use in the production of a medicament for the purpose of treating cancer with radiation optionally in combination with one or more other anticancer agent, such as a check point inhibitor or combination of check point inhibitors.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering a benzodiazepine derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 7-ethynyl-1-methyl-5-phenyl-1,3-dihydro-2H-benzo[e][1,4]diazepin-2-one (QH-II-066) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 7-ethynyl-5-(2-fluorophenyl)-1-methyl-1,3-dihydro-2H-benzo[e][1,4]diazepin-2-one (KRM-II-08) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4H-benzo[f]imidazo[1,5-a][1,4]diazepin-3-yl)oxazole (KRM-II-18B) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)oxazole (KRM-II-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-phenyl-4H-benzo[f]imidazo[1,5-a][1,4]diazepin-3-yl)oxazole (KRM-II-82) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-(pyridin-2-yl)-4H-benzo[f]imidazo[1,5-a][1,4]diazepin-3-yl)-3-methyl-1,2,4-oxadiazole (MP-III-085) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 3-ethyl-5-(8-ethynyl-6-(pyridin-2-yl)-4H-benzo[f]imidazo[1,5-a][1,4]diazepin-3-yl)-1,2,4-oxadiazole (MP-III-080) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering ethyl 8-ethynyl-6-phenyl-4H-benzo[f]imidazo[1,5-a][1,4]diazepine-3-carboxylate (XHe-II-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering ethyl 8-ethynyl-6-(pyridin-2-yl)-4H-benzo[f]imidazo[1,5-a][1,4]diazepine-3-carboxylate (HZ-166) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4H-benzo[f]imidazo[1,5-a][1,4]diazepine-3-carboxylate (JY-XHe-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 8-ethynyl-6-(pyridin-2-yl)-4H-benzo[f]imidazo[1,5-a][1,4]diazepine-3-carboxylic acid (SR-II-54) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 8-ethynyl-6-(2-fluorophenyl)-4-methyl-4H-benzo[f]imidazo[1,5-a][1,4]diazepine-3-carbonitrile (MP-III-018A) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 8-ethynyl-6-(2-fluorophenyl)-N,4-dimethyl-4H-benzo[f]imidazo[1,5-a][1,4]diazepine-3-carboxamide (MP-III-022) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4//-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering ethyl 8-ethynyl-6-(2-fluorophenyl)-4-methyl-4H-benzo[f]imidazo[1,5-a][1,4]diazepine-3-carboxylate (SH-053) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL- II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering 8-ethynyl-6-(2-fluorophenyl)-N,N,4-trimethyl-4H-benzo[f]imidazo[1,5-a][1,4]diazepine-3-carboxamide (GL-II-73) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering N-ethyl-8-ethynyl-6-(2-fluorophenyl)-4-methyl-4H-benzo[f]imidazo[1,5-a][1,4]diazepine-3-carboxamide (GL-II-74) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering N-cyclopropyl-8-ethynyl-6-(2-fluorophenyl)-4-methyl-4H-benzo[f]imidazo[1,5-a][1,4]diazepine-3-carboxamide (GL-II-75) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of ipilimumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of pembrolizumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of cemiplimab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of atezolizumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]

imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of nivolumab and ipilimumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of durvalumab.

In certain embodiments, this disclosure relates to methods of treating cancer, brain cancer, brain metastasis, or melanoma brain metastasis comprising the steps of: administering (8-ethynyl-6-(2-fluorophenyl)-4-methyl-4H-benzo[f]imidazo[1,5-a][1,4]diazepin-3-yl) (pyrrolidin-1-yl) methanone (GL-II-76) its derivative or salt thereof to a subject diagnosed with a cancer, brain cancer, brain metastasis, or melanoma brain metastasis; and concurrently or soon thereafter directing radiation to the cancer, brain cancer, brain metastasis, or melanoma brain metastasis; and thereafter administering to the subject an effective amount of avelumab.

Benzodiazepine Derivatives

In certain embodiments, the benzodiazepine derivative is any compound reported herein or derivative thereof. In certain embodiments, the benzodiazepine derivative is any compound reported herein or such compound substituted with one or more, the same or different, substituents. In certain embodiments, the benzodiazepine derivative is a compound of formula I:

Formula I

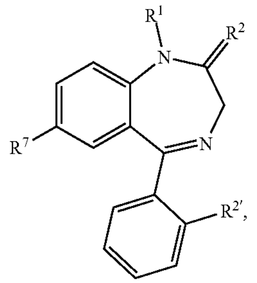

or salt thereof, wherein $R^1$ is alkyl or heterocyclyl optionally substituted with one or more, the same or different $R^3$; $R^2$ is O, or $R^2$ and $R^1$ and the attached atoms come together to form a heterocyclyl optionally substituted with one or more, the same or different $R^3$; $R^{2'}$ is hydrogen or halogen; $R^3$ is alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, benzyl, benzoyl, carbocyclyl, aryl, or heterocyclyl, wherein $R^3$ is optionally substituted with one or more, the same or different, $R^4$; and $R^4$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, or heterocyclyl; and $R^7$ is halogen or alkynyl.

In certain embodiments, $R^1$ is alkyl.

In certain embodiments, $R^1$ is methyl.

In certain embodiments, $R^2$ is oxygen.

In certain embodiments, $R^{2'}$ is hydrogen or fluoro.

In certain embodiments, $R^7$ is alkynyl.

In certain embodiments, $R^7$ is ethynyl.

In certain embodiments, $R^1$ is alkyl, $R^2$ is oxygen, $R^{2'}$ is hydrogen or fluoro, $R^7$ is alkynyl.

In certain embodiments, the benzodiazepine derivative is a compound of formula IA:

Formula IA

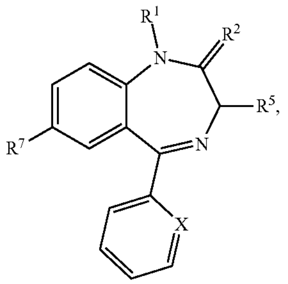

or salt thereof, wherein X is N or C—$R^{2'}$; $R^1$ is alkyl or heterocyclyl optionally substituted with one or more, the same or different $R^3$; $R^2$ is O, or $R^2$ and $R^1$ and the attached atoms come together to form a heterocyclyl optionally substituted with one or more, the same or different $R^3$; $R^{2'}$ is hydrogen or halogen; $R^3$ is alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, (alkyl)$_2$amino, benzyl, benzoyl, carbocyclyl, aryl, or heterocyclyl, wherein $R^3$ is optionally substituted with one or more, the same or different, $R^4$; and $R^4$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N, N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, or heterocyclyl; $R^5$ is hydrogen or alkyl; and $R^7$ is halogen or alkynyl.

In certain embodiments, the benzodiazepine derivative is a compound of formula IB Formula IB

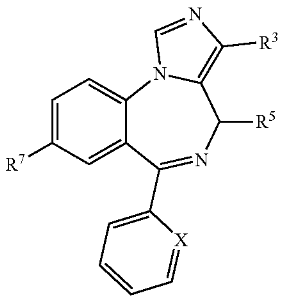

or salt thereof, wherein X is N or C—$R^{2'}$; $R^{2'}$ is hydrogen or halogen; $R^3$ is alkyl, alkenyl, alkynyl, alkanoyl, halogen, nitro, cyano, hydroxy, amino, amido, mercapto, formyl, carboxy, carbamoyl, azido, alkoxy, alkylthio, alkylamino, $(alkyl)_2$amino, benzyl, benzoyl, carbocyclyl, aryl, or heterocyclyl wherein $R^3$ is optionally substituted with one or more, the same or different, $R^4$; $R^4$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, or heterocyclyl; $R^5$ is hydrogen or alkyl; and $R^7$ is halogen or alkynyl.

In certain embodiments, $R^3$ is alkyl, carboxy, carbamoyl, or heterocyclyl optionally substituted.

In certain embodiments, $R^3$ is oxazolyl or oxadiazolyl optionally substituted.

In certain embodiments, the benzodiazepine derivative is 7-ethynyl-1-methyl-5-phenyl-1,3-dihydro-2H-benzo[e][1,4]diazepin-2-one (QH-II-066), its derivative or salt thereof.

In certain embodiments, the benzodiazepine derivative is 7-ethynyl-5-(2-fluorophenyl)-1-methyl-1,3-dihydro-2H-benzo[e][1,4]diazepin-2-one (KRM-II-08), its derivative or salt thereof.

In certain embodiments, the benzodiazepine derivative is 5-(8-ethynyl-6-(2-fluorophenyl)-4H-benzo[f]imidazo[1,5-a][1,4]diazepin-3-yl)oxazole (KRM-II-18B), its derivative or salt thereof.

In certain embodiments, the benzodiazepine derivative is 5-(8-ethynyl-6-(pyridin-2-yl)-4H-benzo[f]imidazo[1,5-a][1,4]diazepin-3-yl)oxazole (KRM-II-81), its derivative or salt thereof.

In certain embodiments, the benzodiazepine derivative is 5-(8-ethynyl-6-phenyl-4H-benzo[f]imidazo[1,5-a][1,4]diazepin-3-yl)oxazole (KRM-II-82), its derivative or salt thereof.

In certain embodiments, the benzodiazepine derivative is 5-(8-ethynyl-6-(pyridin-2-yl)-4H-benzo[f]imidazo[1,5-a][1,4]diazepin-3-yl)-3-methyl-1,2,4-oxadiazole (MP-III-085), its derivative or salt thereof.

In certain embodiments, the benzodiazepine derivative is 3-ethyl-5-(8-ethynyl-6-(pyridin-2-yl)-4H-benzo[f]imidazo[1,5-a][1,4]diazepin-3-yl)-1,2,4-oxadiazole (MP-III-080), its derivative or salt thereof.

In certain embodiments, the benzodiazepine derivative is ethyl 8-ethynyl-6-phenyl-4H-benzo[f]imidazo[1,5-a][1,4]diazepine-3-carboxylate (XHe-II-053), its derivative or salt thereof.

In certain embodiments, the benzodiazepine derivative is ethyl 8-ethynyl-6-(pyridin-2-yl)-4H-benzo[f]imidazo[1,5-a][1,4]diazepine-3-carboxylate (HZ-166), its derivative or salt thereof.

In certain embodiments, the benzodiazepine derivative is ethyl 8-ethynyl-6-(2-fluorophenyl)-4H-benzo[f]imidazo[1,5-a][1,4]diazepine-3-carboxylate (JY-XHe-053), its derivative or salt thereof.

In certain embodiments, the benzodiazepine derivative is 8-ethynyl-6-(pyridin-2-yl)-4H-benzo[f]imidazo[1,5-a][1,4]diazepine-3-carboxylic acid (SR-II-54), its derivative or salt thereof.

In certain embodiments, the benzodiazepine derivative is 8-ethynyl-6-(2-fluorophenyl)-4-methyl-4H-benzo[f]imidazo[1,5-a][1,4]diazepine-3-carbonitrile (MP-III-018A), its derivative or salt thereof.

In certain embodiments, the benzodiazepine derivative is 5-(8-ethynyl-6-(2-fluorophenyl)-4-methyl-4H-benzo[f]imidazo[1,5-a][1,4]diazepin-3-yl)-3-isopropyl-1,2,4-oxadiazole (GL-I-81), its derivative or salt thereof.

In certain embodiments, the benzodiazepine derivative is 3-ethyl-5-(8-ethynyl-6-(2-fluorophenyl)-4-methyl-4H-benzo[f]imidazo[1,5-a][1,4]diazepin-3-yl)-1,2,4-oxadiazole (GL-I-66), its derivative or salt thereof.

In certain embodiments, the benzodiazepine derivative is 5-(8-ethynyl-6-(2-fluorophenyl)-4-methyl-4H-benzo[f]imidazo[1,5-a][1,4]diazepin-3-yl)-3-methyl-1,2,4-oxadiazole (GL-I-65), its derivative or salt thereof.

In certain embodiments, the benzodiazepine derivative is 8-ethynyl-6-(2-fluorophenyl)-N,4-dimethyl-4H-benzo[f]imidazo[1,5-a][1,4]diazepine-3-carboxamide (MP-III-022), its derivative or salt thereof.

In certain embodiments, the benzodiazepine derivative is ethyl 8-ethynyl-6-(2-fluorophenyl)-4-methyl-4H-benzo[f]imidazo[1,5-a][1,4]diazepine-3-carboxylate (SH-053), its derivative or salt thereof.

In certain embodiments, the benzodiazepine derivative is 8-ethynyl-6-(2-fluorophenyl)-N,N,4-trimethyl-4H-benzo[f]imidazo[1,5-a][1,4]diazepine-3-carboxamide (GL-II-73), its derivative or salt thereof.

In certain embodiments, the benzodiazepine derivative is N-ethyl-8-ethynyl-6-(2-fluorophenyl)-4-methyl-4H-benzo[f]imidazo[1,5-a][1,4]diazepine-3-carboxamide (GL-II-74), its derivative or salt thereof.

In certain embodiments, the benzodiazepine derivative is N-cyclopropyl-8-ethynyl-6-(2-fluorophenyl)-4-methyl-4H-benzo[f]imidazo[1,5-a][1,4]diazepine-3-carboxamide (GL-II-75), its derivative or salt thereof.

In certain embodiments, the benzodiazepine derivative is (8-ethynyl-6-(2-fluorophenyl)-4-methyl-4H-benzo[f]imidazo[1,5-a][1,4]diazepin-3-yl) (pyrrolidin-1-yl) methanone (GL-II-76), its derivative or salt thereof.

The term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom, replacing a sulfur atom with an oxygen atom, replacing an amino group with a hydroxyl group, replacing a hydroxyl with group an amino group, replacing a protonated carbon (CH) with a nitrogen in an aromatic ring, replacing a bridging amino group (—NH—) with an oxy group (—O—), or vice versa. The derivative may be a prodrug. The derivative may be the compound conjugated to itself through a linking group as a dimer. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $—NR_aR_b$, $—NR_aC(=O)R_b$, $—NR_aC(=O)NR_aNR_b$, $—NR_aC(=O)OR_b$, $—NR_aSO_2R_b$, $—C(=O)R_a$, $—C(=O)OR_a$, $—C(=O)NR_aR_b$, $—OC(=O)NR_aR_b$, $—OR_a$, $—SR_a$, $—SOR_a$, $—S(=O)_2R_a$, $—OS(=O)_2R_a$ and $—S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

"Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., $—S—CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers to an alkyl group as defined above attached through an amino bridge. An example of an alkylamino is methylamino, (i.e., $—NH—CH_3$).

"Alkanoyl" refers to an alkyl as defined above attached through a carbonyl bridge (i.e., —(C=O) alkyl).

Checkpoint Inhibitors

In certain embodiment, checkpoint inhibitor is a biologic therapeutic or a small molecule. In certain embodiment, checkpoint inhibitor is a monoclonal antibody, a humanized antibody, a fully human antibody, a fusion protein or a combination thereof. In certain embodiment, checkpoint inhibitor is a PD-1, a PDL-1 and/or a CTLA-4 checkpoint inhibitor. In certain embodiment, checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof.

In certain embodiment, checkpoint inhibitor is selected from ipilimumab (anti-CTLA-4 antibody), nivolumab, pembrolizumab, and cemiplimab (anti-PD-1 antibodies), atezolizumab, durvalumab, and avelumab (anti-PD-L1 antibody).

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In certain embodiments, the checkpoint inhibitor is an CTLA-4 antibody such as ipilimumab, an anti-PD-1 antibody such as pembrolizumab, nivolumab, REGN2810, BMS-936558, SHR1210, IBI308, PDR001, BGB-A317, BCD-100, and JS001 or an anti-PD-L1 such as avelumab, atezolizumab, durvalumab, and KN035. In certain embodiments, administering to the subject an effective amount of a checkpoint inhibitor is a combination of an anti-CTLA-4 antibody and an anti-PD-1 antibody.

Radiation Enhances Melanoma Response to Immunotherapy and Synergizes with Benzodiazepines to Promote Anti-Tumor Activity Experiments indicate that radiotherapy (RT) followed by treatment with immune checkpoint inhibitors improves melanoma brain metastases (MBM) patient survival compared to other combination strategies. RNA-seq of MBM tumors exhibit overrepresentation of genes implicated in NFkB signaling. There is also expression of $GABA_A$ receptor subunits across both treatment groups. Melanoma cells express functional $GABA_A$ receptors and benzodiazepines impair tumor growth. Combination of sub-lethal radiotherapy doses with benzodiazepine derivatives results in significant ipsilateral and out of field abscopal (other location) anti-tumor activity, which is associated with enhanced tumor infiltration with poly-functional CD8 T-cells. This study provides evidence that radiotherapy enhances treatment response to immune checkpoint inhibitors and synergizes with benzodiazepines to promote anti-tumor activity.

Stereotactic radiosurgery (SRS) is effective in promoting local response by delivering a potentially tumor lethal dose and sparing healthy brain. Survival analysis of a heterogeneous group of MBM patients who received radiation therapy first followed by immune checkpoint inhibitors had improved survival compared to other strategies. Using the B16F10-GP melanoma murine model, experiments indicate that radiation therapy first followed by immune checkpoint inhibitors improves survival. RNA-seq of resected tumors from MBM patients was performed. This analysis revealed expression of GABR genes, which code for subunits of the gamma-aminobutyric acid (GABA) neurotransmitter receptor ($GABA_AR$). Treatment of B16F10-GP tumor bearing mice with a benzodiazepine, a $GABA_AR$ positive allosteric modulator, reduced tumor growth, which was enhanced with concurrent radiation promoting both ipsilateral and abscopal anti-tumor activity. This treatment effect was associated with increased tumor infiltration with effector CD8 T cells that exhibited enhanced poly-functionality.

Impact of Timing of Immunotherapy and Radiation in Patients with Melanoma Brain Metastases.

A retrospective analysis was conducted with resected MBM who received CNS-directed radiation therapy (RT) (n=8) or immune checkpoint inhibitor(s) (ICI) (pembrolizumab, nivolumab, and/or ipilimumab) and RT (n=17). Overall, the patient population represents a heterogeneous with differences in number of metastatic lesions, aspects of treatment including BRAF-inhibitor use, as well as genetic background (e.g., BRAF status). a Kaplan-Meier survival analysis of this patient population and find those patients was conducted. Those who received both ICI and RT had superior survival compared to patients receiving RT alone. Those patients who received both ICI and RT were stratified into two treatment groups: (1) patients receiving radiation therapy (RT) followed by immune checkpoint inhibitors (ICI) (RT-ICI) (n=11); (2) patients receiving ICI followed by RT and then ICI again (ICI-RT) (n=6), where RT was either stereotactic radiosurgery (SRS), n=15; or whole-brain radiation therapy (WBRT), n=2. Survival analysis suggests that the RT-ICI treatment group had an improved outcome. The survival curves show modest evidence of significance considering the small sample size. At 15 months, a separation was observed in Kaplan-Meier curves for the 'timing' analysis, though the small sample size precludes our further testing the significance of this result.

Patient tumors (FFPE: formalin fixed paraffin embedded) from the two treatment groups (RT-ICI and ICI-RT) were macro-dissected, excluding brain and minimizing the amount of necrosis using a corresponding H&E-stained slide. There was sufficient resected MBM tissue from FFPE for sequencing (RNA-seq using Transcriptome Capture). Differential gene expression analysis with SAMseq™, conducted without restriction or assumption, between the RT-ICI and ICI-RT treatment groups showed 48 deregulated genes, all of which were increased in expression in the RT-ICI group. Annotation/pathway enrichment analysis using MetaCore™ revealed a significant enrichment of genes that are functionally involved in apoptosis and anti-apoptotic signaling, including: NIK (MAP3K14), the key modulator of non-canonical NFkB signaling which activates p52, a non-TAF transcriptional coactivator that mediates activator-dependent transcription by RNA pol II, and assembly for RelB; RIPK1, a receptor interacting kinase which also participates in NFkB as well as JNK and Akt signaling pathways; and DAB2. Overall, enriched pathways include genes involved in immunity and particularly prevalent are NFkB pathway interacting proteins. Together, these results suggest that RT may activate cell intrinsic pathways involved in para-inflammation and apoptosis, and that these may contribute to improved response and survival for the subsequent ICI.

Figure 1B:
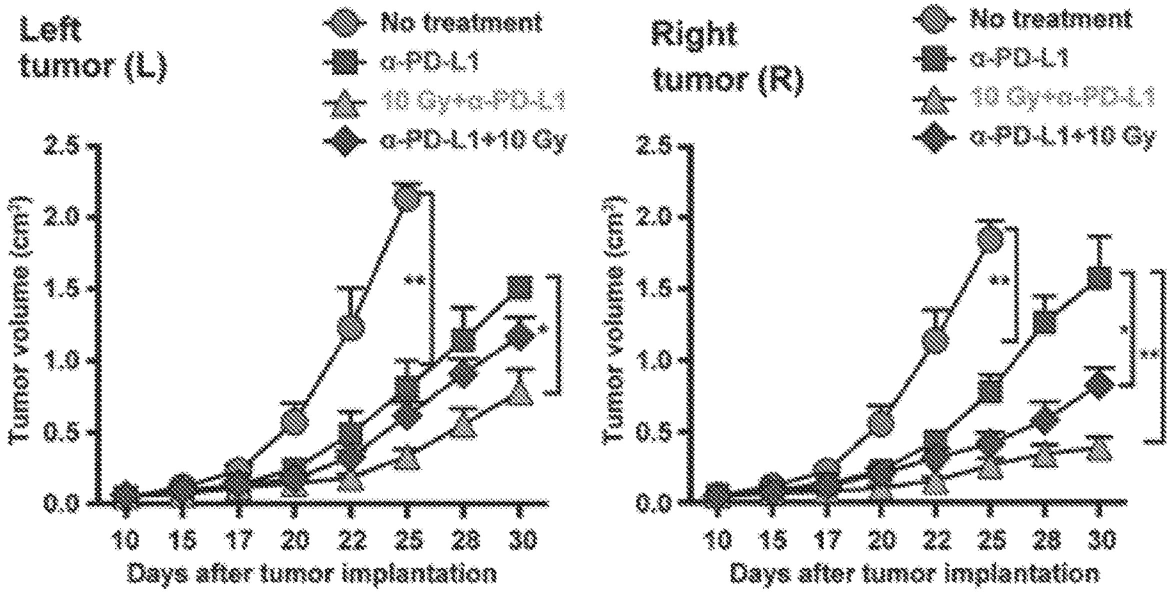

Sequential Administration of Radiation and Anti-PD-L1 Improves Anti-Tumor Activity In Vivo The clinical observation of improved outcome for RT-ICI was analyzed using a murine model. B16F10-GP cells ($0.5\times10^5$) were implanted in both right and left flanks of C57BL/6 mice (FIG. 1A). A single dose of radiation at 10 Gy was delivered to the right flank only using a 0.5 cm bolus material, on Day 10 after implanting the melanoma cells. Day 10 was chosen to allow for growth of tumor cells in flanks to the point where they became palpable. After irradiation, tumor kinetics were observed with: (i) no treatment control; (ii) anti-PD-L1 alone; (iii) 10 Gy administered on Day 10 (in the morning) before anti-PD-L1 (RT-ICI) (in the evening); (iv) anti-PD-L1 administered first, followed by 10 Gy administered on Day 20 (ICI-RT). Anti-PD-L1 was given by intraperitoneal injection every third day. The best tumor control within the irradiated volume and the non-irradiated region (the 'abscopal site') was noted for RT-ICI, when 10 Gy was administered before same day anti-PD-L1 treatment (FIG. 1B), consistent with the observation in patients that RT-ICI has an improved outcome. No anti-tumor activity was observed when CD8 T cells were depleted, indicating that T cells were necessary for responses to anti-PD-L1 therapy.

Melanoma Cell Autonomous Expression of Functional $GABA_AR$ is a Therapeutic Vulnerability The RNA-seq data of the 17 MBM tumor samples was surveyed for genes whose expression appeared overrepresented in both RT-ICI and ICI-RT treatment groups and which could serve as potential therapeutically vulnerable target(s). This analysis revealed that genes coding for $GABA_AR$ subunits (GABR genes) in MBM tumors were overrepresented and none of the GABR genes were found to be differentially expressed across the treatment groups when conducting SAMseq™ differential expression analysis.

$GABA_AR$ forms a hetero-pentameric complex composed most commonly of two α, two β, and γ subunits encoded by GABRA (1-6), GABRB (1-3), and GABRG (1-3), respectively, to which a significant number of FDA-approved compounds bind, including barbiturates, neurosteroids, anesthetics, alcohols, and benzodiazepines. RT-PCR analysis was conducted for GABR expression in four patient derived metastatic melanoma cell lines (A375, RPMI-7951, SKMEL-24, SKMEL-28). All these lines express to a varying degree GABRA3, while SKMEL-24 and SKMEL-28 have uniquely high GABRA2 and GABRA5 expression, respectively. There is significantly less expression of GABRB1-3 and GABRG1-3 in the human melanoma cell lines compared to GABRA levels. Western blotting was performed of human melanoma cell line A375 and murine line B16F10 for subunits α2, α3 and α5 given the higher levels of expression identified by RT-PCR. A375 shows reactivity for α2 and α3, to varying degrees, but an absence of α5, consistent with RT-PCR results. In contrast, B16F10 does have α5, as well as α2 and α3.

$GABA_AR$ is an anion (Cl−) channel that changes the transmembrane potential of cells, either depolarizing or hyperpolarizing depending upon channel directionality and activity of other membrane transport protein. To establish autonomous expression of $GABA_AR$ subunits in melanoma cell lines results in assembly of a functional ligand-dependent channel, electrophysiological testing was performed in human melanoma (A375) and murine (B16F10) lines. Patch clamp currents were recorded for A375 and B16F10. Both lines exhibited a response to the $GABA_AR$ native agonist, the neurotransmitter GABA. Compared to the A375 cell line, the B16F10 cells exhibited a larger maximal response to and a greater affinity for GABA (2.8+0.2 (n=6) vs 8.4±3.8 μM (8) and −430±70 (n=6) vs −230±41 (n=8) pA), respectively, where EC50 is the concentration of drug that elicits the half maximal current. the effect of benzodiazepines on current of A375 and B16F10 cells was tested. A fully functional benzodiazepine binding site requires assembly of a $GABA_AR$ with a canonical αβαβγ subunit stoichiometry. Benzodiazepine binding at the α-γ interface increases the probability of the channel opening in the presence of GABA and increases the number of anions crossing the membrane.

Figure 2A:
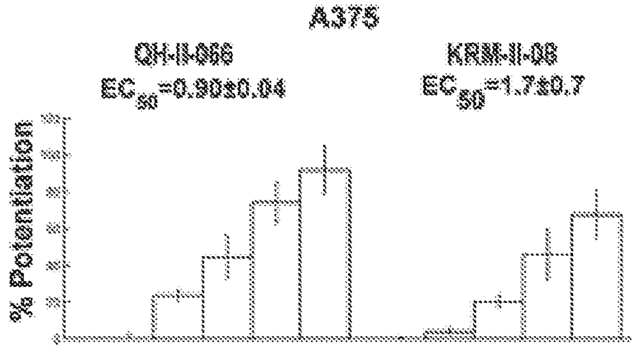
FIG. 2A shows data on the potentiation of A375 cells in response to benzodiazepines (QH-II-066 and KRM-II-08) recorded using electrophysiology ([GABA]=1 μM; [Benzodiazepine]=0, 0.3, 1, 3, 10 μM).
Figure 2B:
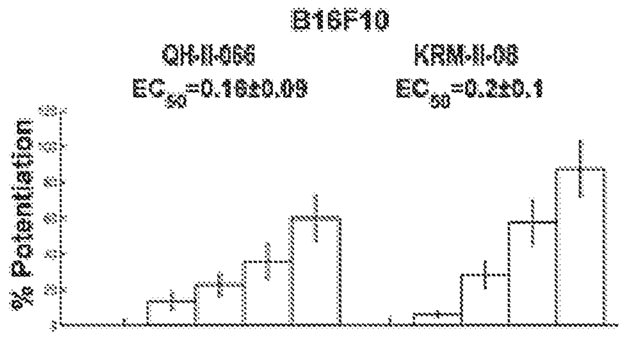
FIG. 2B shows data on the potentiation of B16F10 cells in response to benzodiazepines (QH-II-066 and KRM-II-08) recorded using electrophysiology ([GABA]=1 μM; [Benzodiazepine]=0, 0.3, 1, 3, 10 μM).

Two benzodiazepines were tested (QH-II-066 and KRM-II-08). QH-II-066 and KRM-II-08 differ in having H and F at R2' of the benzene ring of benzodiazepine, respectively. Both QH-II-066 and KRM-II-08 enhance the effect of GABA in a dose-dependent manner in A375 and B16F10 (B16F10: EC50 KRM-II-08 and QH-II-066 values of 0.2±0.1 μM and 0.16±0.09 UM, respectively; A375: $EC_{50}$ KRM-II-08 and QH-II-066 values of 1.7±0.2 μM and 0.9±0.4 μM, respectively) (FIG. 2A, 2B).

Electrophysiology results also indicate that both QH-II-066 and KRM-II-08 act as GABAAR positive allosteric modulators, increasing membrane anion permeability. Further, the micromolar EC50s obtained indicate that these receptors are more likely to be synaptic isoforms (α1, 2 or 3) and not supersensitive extra synaptic isoforms (α4 or 5), consistent overall with RT-PCR and Western blots.

The electrophysiology whole-cell patch clamp experiments occur within a minute. In studies of the pediatric brain cancer medulloblastoma, sustained incubation of medulloblastoma cancer cells with QH-II-066 and KRM-II-08 can impair the cells viability in vitro and reduce tumor volume in a xenograft mouse model using patient derived medulloblastoma cells. These benzodiazepines exhibit more than an order of magnitude improved effectiveness in impairing cell viability versus diazepam. To determine their effect on melanoma cell survival, A375 and B16F10 were treated with QH-II-066, KRM-II-08, or diazepam for 48 hours. A dose-dependent reduction in cell viability was observed in both cell lines with KRM-II-08 ($IC_{50}$: A375, 1.33±0.08 μM; B16F10, 6.1±0.8 μM) and QH-II-066 ($IC_{50}$: A375, 2.7±0.2μ; B16F10, 8.2±0.9μ). In contrast, diazepam had no effect on the viability of either A375 or B16F10 cells. Similar $IC_{50}$ values were obtained for additional human metastatic melanoma lines treated with QH-II-066 and KRM-II-08. Cell lines which showed no significant response to the benzodiazepines were those where TP53 was mutated, consistent with studies in medulloblastoma which showed a contributing role of p53 to the mechanism of benzodiazepine-induced apoptosis.

To determine whether the effect on cell survival was benzodiazepine-specific, we tested allopregnanolone which is also a positive allosteric modulator of $GABA_AR$, but a non-benzodiazepine neurosteroid that does not bind at the canonical high affinity benzodiazepine binding site located on the α-γ interface. Allopregnanolone does not impair the viability of A375 and B16F10 lines, suggesting that the effect on melanoma cell survival is benzodiazepine-specific or at least specific to the higher affinity benzodiazepine-derivatives tested (QH-II-066 and KRM-II-088).

Changes induced by the benzodiazepine as a consequence of creating a net efflux of chloride anion, included an upregulation of TP53 and a depolarization of the mitochondrial transmembrane potential, ultimately resulting in apoptosis via the intrinsic mitochondria-mediated pathway. Thus, Experiments were performed to determine if benzodiazepine elicited a similar response in A375 and B16F10 cells. QH-II-066 enhanced expression of p53 and rapid (within 10 minutes) depolarization of the mitochondrial transmembrane potential, which may lead to activation of apoptosis in melanoma cells.

Benzodiazepine Reduces Tumor Volume and Synergizes with Radiation In Vivo

Figure 3A:
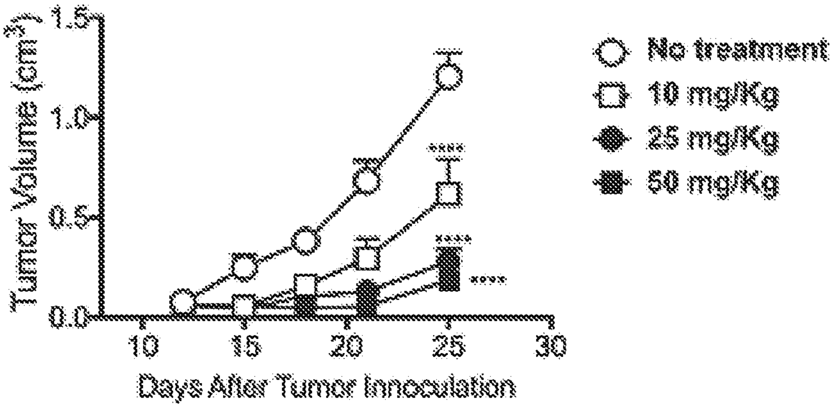
FIGS. 3A-D show data on the impact of benzodiazepine on tumor volume and its effectiveness in combination with radiation.
Figure 3B:
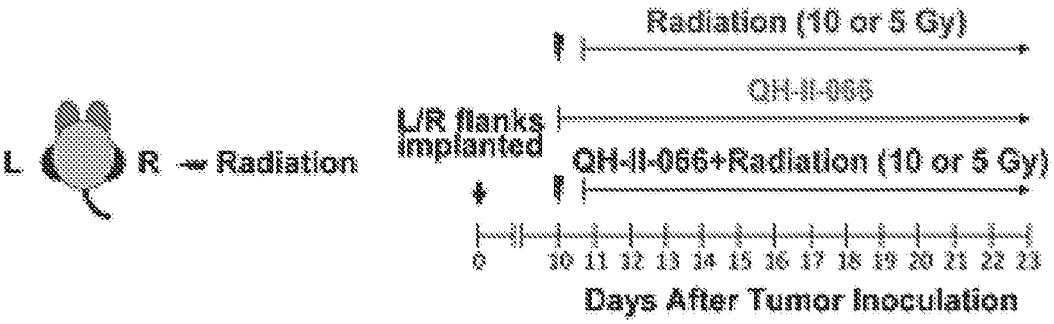

Since melanoma cell viability in vitro was impaired by benzodiazepines QH-II-066 and KRM-II-08, experiments were performed to determine if benzodiazepine had anti-tumor activity in vivo. QH-II-066 was used for in vivo testing given that this compound has previously been tested in non-human primates without any adverse side effects or toxicity. Using QH-II-066, a dose-dependent reduction in B16F10-GP tumor growth was observe (10, 25, and 50 mg/kg) (FIG. 3A). There is a negligible difference between 25 and 50 mg/kg, indicating that a lower dose of the benzodiazepine is sufficient for anti-tumor activity in an otherwise aggressive melanoma model. Given that immune checkpoint inhibitor efficacy is enhanced by radiation therapy, experiments were performed to determine whether RT combined with QH-II-066 synergize to control ipsilateral and abscopal tumor volume using the B16F10-GP syngeneic melanoma murine model. B16F10-GP melanoma cells were implanted ($0.5\times10^5$) in both right and left flanks of C57BL/6 mice (FIG. 3B). A single dose of radiation (either 10 or 5 Gy) was delivered to the right flank on Day 10 after implanting of B16F10-GP cells. After irradiation, tumor kinetics were observed with: (i) no treatment control; (ii) QH-II-066 alone at 10 mg/kg; (iii) radiation alone (10 or 5 Gy); (iv) 10 or 5

Figure 3C:
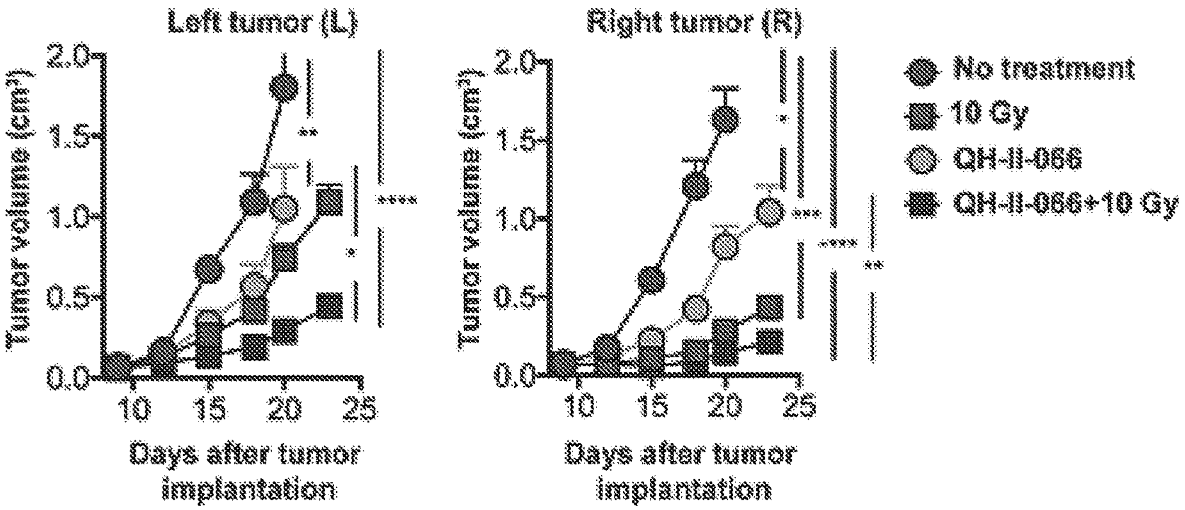
Figure 3D:
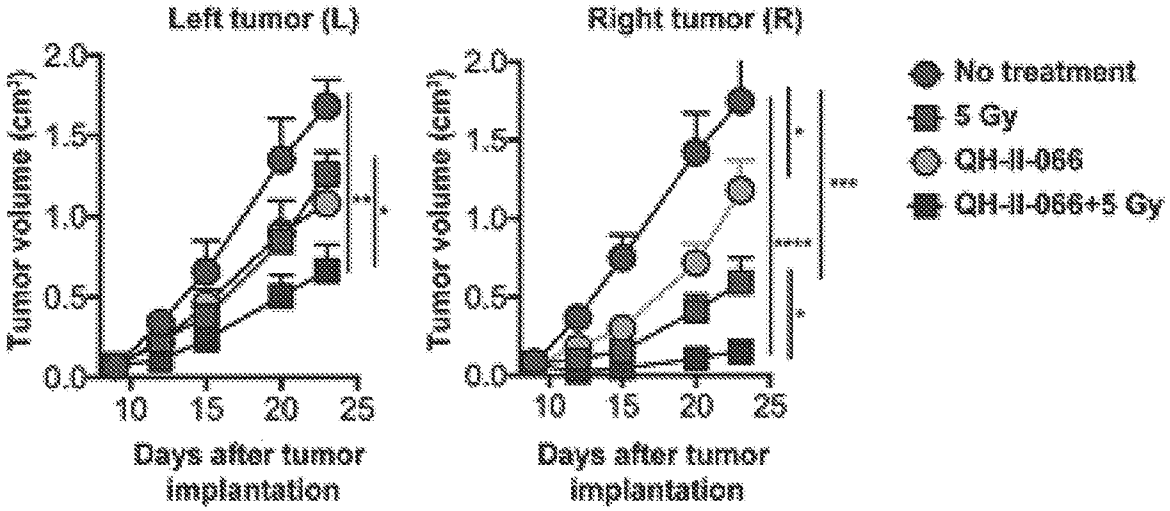
Figure 4A:
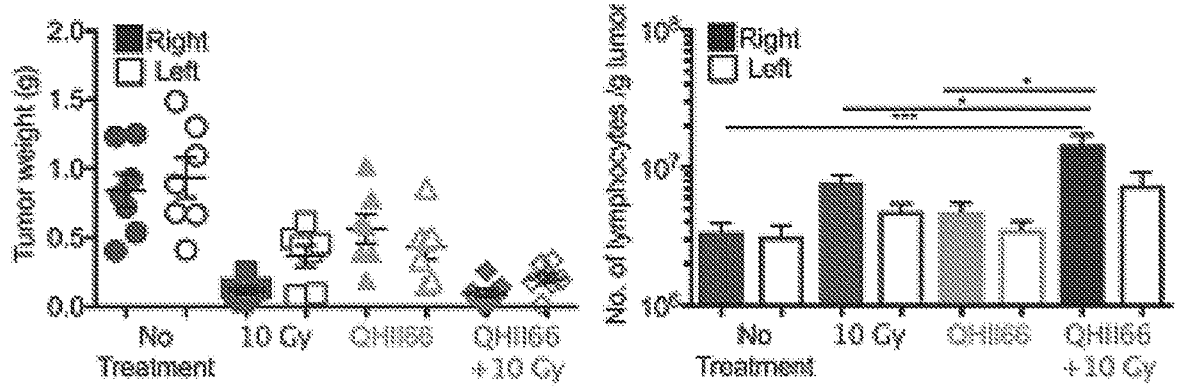
FIGS. 4A-4E show data on the impact of benzodiazepine and radiation on CD8 response in tumors of mice.
Figure 4B:
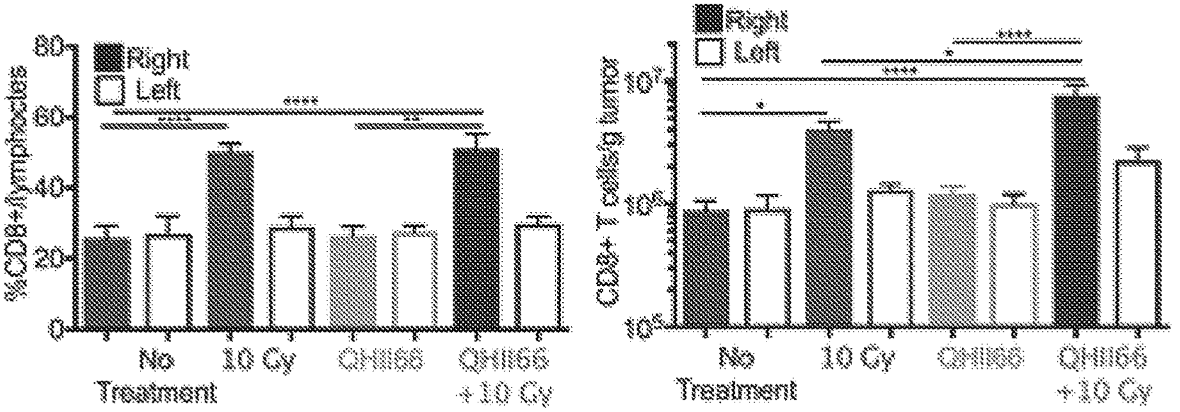
Figure 4C:
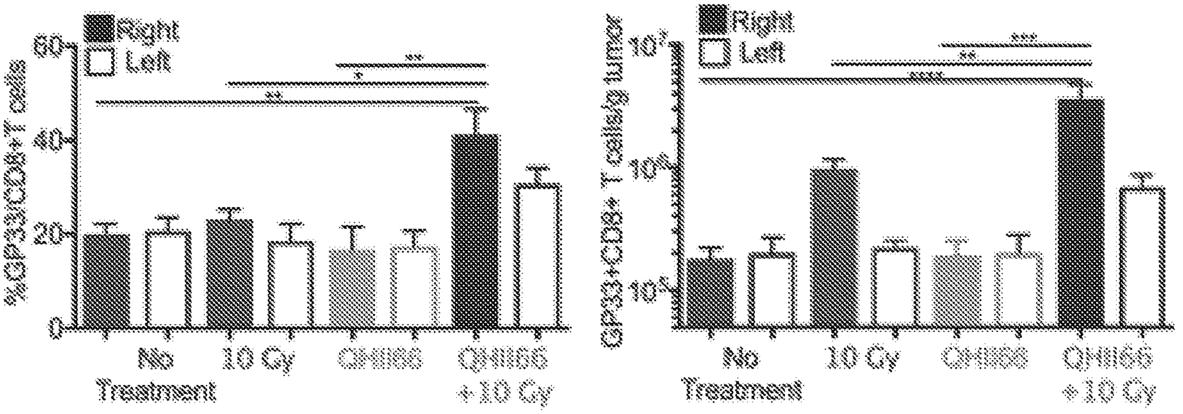
Figure 4D:
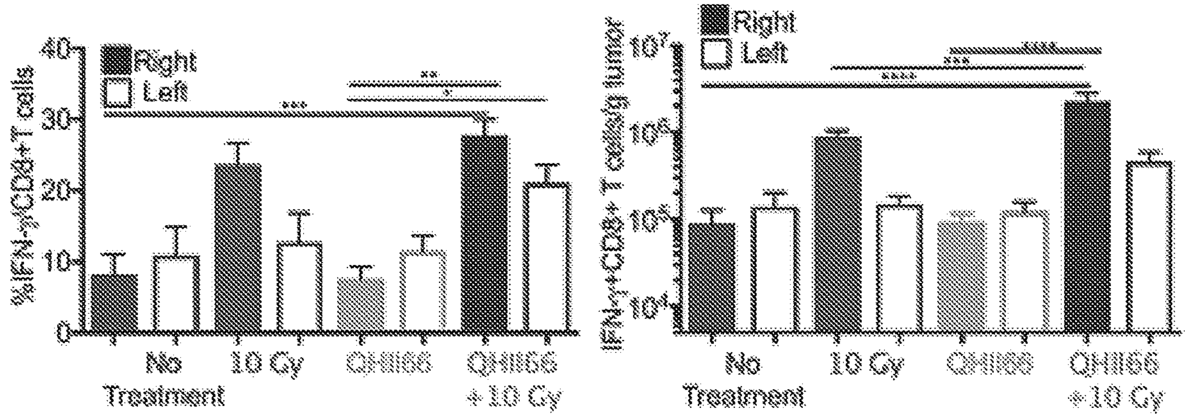
Figure 4E:
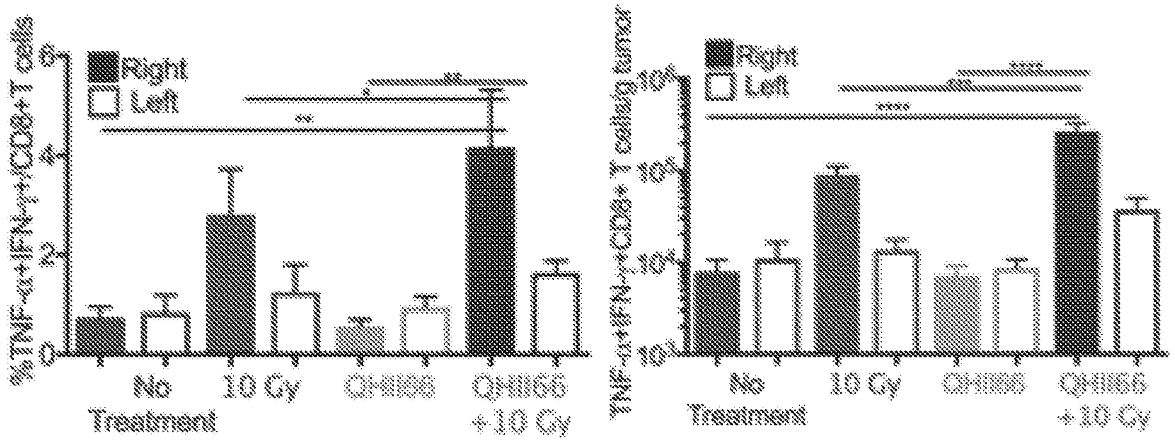

Gy on Day 10 (in the morning) followed by QH-II-066 (10 mg/kg, in the evening). QH-II-066 (10 mg/kg) was used so that if there was enhanced efficacy in combination with radiation therapy, one could clearly discern a response since 10 mg/kg once daily of QH-II-066 on its own did not have as pronounced an effect as 25 mg/kg, a concentration which appears to achieve maximal effect on the tumor. The combination of radiation therapy and QH-II-066 at 10 mg/kg showed a strongly synergistic anti-tumor effect on the ipsilateral and contralateral tumor, indicating enhanced abscopal activity (FIG. 3C-3D). There was no difference when using different radiation doses (10 or 5 Gy).

To determine whether these apparent synergistic effects were mediated by an enhanced immune response, immunophenotyping of bilateral tumors was performed. Compared to vehicle, radiation with 10 or 5 Gy or in combination with QH-II-066 induced enhanced infiltration of CD8+ T cells in the ipsilateral tumor, while QH-II-066 alone did not induce CD8+ T cell infiltration. While the overall number of CD8+ T cells was not significantly increased in the contralateral tumor, significant increase in antigen-specific, poly-functional T cells (expressing IFN-γ and TNF-a) was observed in both ipsilateral and contralateral tumors treated with a combination of (ipsilateral) radiation therapy+systemic QH-II-066. (FIG. 4A-4E). Together, these results indicate that QH-II-066 has direct anti-tumor activity, while a combination of radiation therapy and QH-II-066 has synergy with ipsilateral and abscopal anti-tumor activity.

Benzodiazepine and Anti-PD-L1 have a Synergistic Anti-Tumor Response

Figure 5:
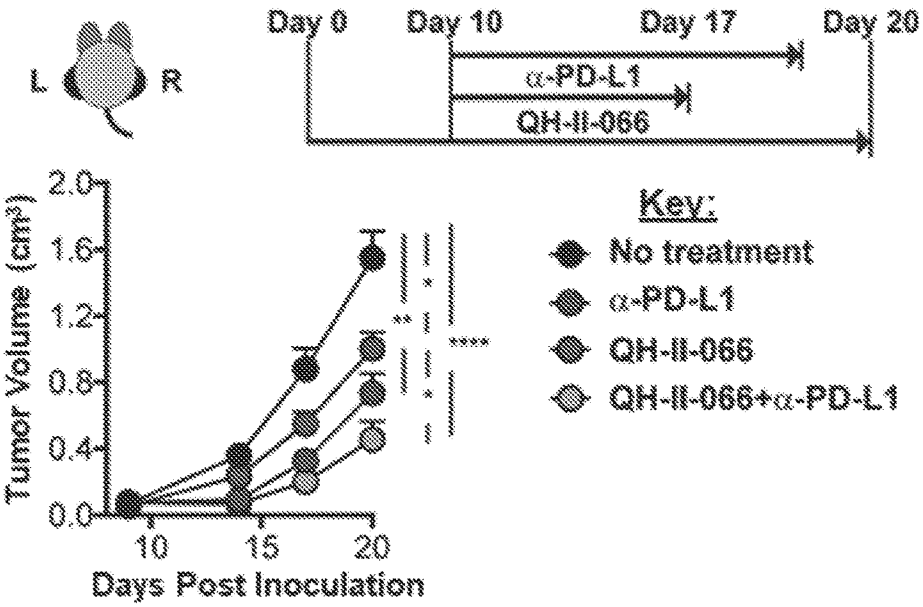
FIG. 5 shows data indicating benzodiazepine potentiates immune checkpoint inhibitor. Mice were implanted in left (L) and right (R) flanks with B16F10-GP tumor cells (Day 0). Day 10, mice received either: (i) no treatment; (ii) QH-II-066; (iii) anti-PD-L1; (iv) QH-II-066 and anti-PD-L1. Effect of combination of QH-II-066 and anti-PD-L1 on tumor growth kinetics. In groups receiving QH-II-066, 10 mg/kg was injected daily for 7 days. In group receiving anti-PD-L1, 200 μg was injected every 3 days through Day 17.

Having observed that QH-II-066 could sensitize a melanoma tumor to radiation and that expression of genes with roles in the cytokine: cytokine receptor interaction pathway was enhanced, experiments were performed to determine if QH-II-066 was capable of potentiating the programmed death ligand 1 immune checkpoint inhibitor (anti-PD-L1). B16F10-GP melanoma cells were implanted in both the right and left flanks of C57BL/6 mice. Day 10 in both the right and left flanks injected i.p.: (i) QH-II-066 (10 mg/kg), then every day for seven days; (ii) anti-PD-L1 (200 μg), then every third day thereafter; (iii) QH-II-066 (10 mg/kg) and anti-PD-L1 (200 μg) at time and frequency detailed for monotherapy treatment groups (FIG. 5). Monotherapy treatment with QH-II-066 or anti-PD-L1 resulted in comparable reductions in tumor volume. The most significant reduction in tumor volume is observed with the dual therapy consisting of QH-II-066 and anti-PD-L1 (FIG. 5). Similar to what was observed for radiation, QH-II-066 and anti-PD-L1 have a synergistic anti-tumor response.

Combined Benzodiazepine, Anti-PD-L1, and Radiotherapy Results in Significant Tumor Regression Having observed potentiation of radiation and anti-PD-L1 by QH-II-066 individually, there might be a more significant tumor response if we administered a 'combo' consisting of radiation (5 Gy), anti-PD-L1, plus QH-II-066. As before, B16F10-GP melanoma cells were implanted in both the right and left flanks of C57BL/6 mice (FIG. 5). The following experimental groups were tested: (i) vehicle alone control; (ii) QH-II-066 alone (10 mg/kg); (iii) a single morning dose of radiation (5 Gy) delivered to the right flank, followed by evening dose of QH-II-066 (10 mg/kg); (iv) anti-PD-L1 plus QH-II-066; (v) a single morning dose of radiation (5 Gy) delivered to the right flank, followed by an evening dose of anti-PD-L1; (vi) a triple or combo therapy, consisting of a single morning dose of radiation (5 Gy) delivered to the right flank, followed by evening doses of anti-PD-L1 plus QH-II-066. After initial i.p. injection of QH-II-066 on Day 10, QH-II-066 was injected i.p. every day for seven days; while anti-PD-L1 was injected i.p. every third day thereafter.

Figure 6:
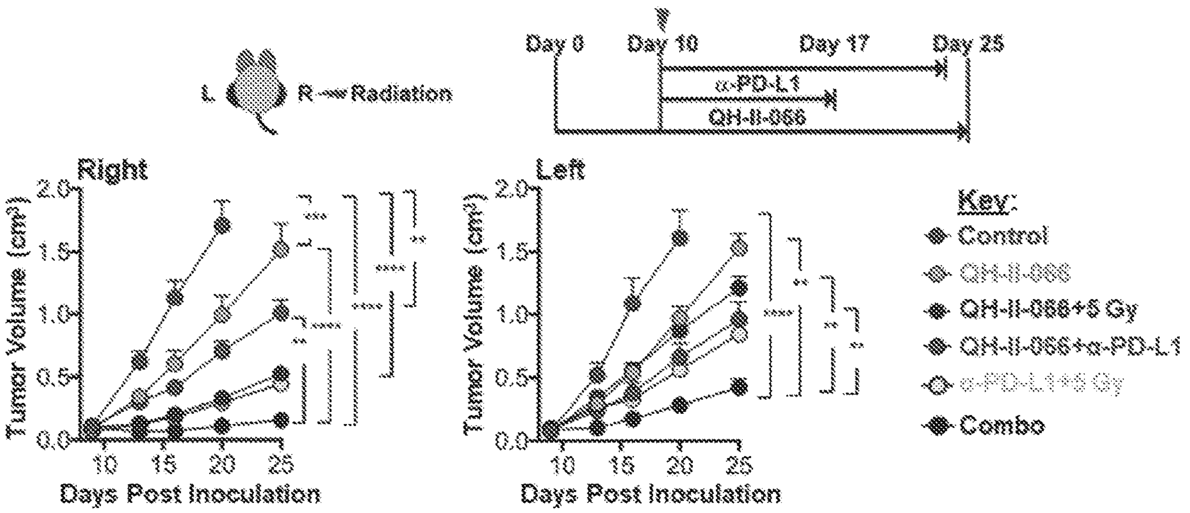
FIG. 6 shows data indicating the effectiveness of polytherapy with benzodiazepine on tumor volume. Mice were implanted in left (L) and right (R) flanks with B16F10-GP tumor cells (Day 0). Day 10, mice received either: (i) vehicle alone; (ii) QH-II-066; (iii) radiation (5 Gy, right flank only) on Day 10 (in the morning), followed by QH-II-066 (in the evening); (iv) QH-II-066 and anti-PD-L1, beginning on day 10; radiation (5 Gy, right flank only) on Day 10 (in the morning), followed by anti-PD-L1 (in the evening). In groups receiving QH-II-066, 10 mg/kg was injected i.p. daily for 7 days. In group receiving anti-PD-L1, 200 μg was injected i.p. every 3 days through the end of experiment or maximum 5 injections.

The dual treatments of benzodiazepine plus radiation or benzodiazepine plus anti-PD-L1 were better than radiation or anti-PD-L1 alone (FIG. 6). Further, right flank tumors which received radiation exhibited greater reduction in tumor growth in treatments including radiation than the left flank tumors, as expected based on above. There is again a pronounced abscopal effect for left non-irradiated flank tumors, as noted above. The most significant ipsilateral and abscopal effect is seen in the combo treatment group, complete tumor regression in some animals (FIG. 6). QH-II-066 plus radiation plus anti-PD-L1 have a synergistic anti-tumor response as well as a potent abscopal effect in combination.

Mouse Experiments

B16F10-GP cell line was grown in Dulbecco's Modified Eagle's medium (DMEM) supplemented with 10% Fetal Bovine Serum, 100 U/mL penicillin and 100 μg/mL streptomycin, 2 mM glutamine. Cells were cultured at 37° C. with 5% $CO_2$.

B16F10-GP melanoma cells ($5\times10^5$) were implanted in Matrigel™ (25%) on right and left flank of 6-8 week old female C57BL/6 mice (Jackson Laboratories, Bar Harbor, ME). Mice were used in accordance with the Emory University Institutional Animal Care and Use Committee guidelines. After the tumors were palpable (10 days), mice were irradiated on right side with a Superflab™ bolus (0.5 cm tissue equivalent material) placed over the tumor, and thereafter tumor measurements taken as indicated. Measurements of left tumor are indicative of abscopal response. Irradiation was done using an X-RAD 320 irradiation unit, a self-contained X-ray system for delivering a precise radiation dosage. The light beam (<8 $mm^2$) was focused on the tumor (right flank only) and mice were irradiated while under anesthesia. Tumor diameters were measured using calipers. Tumor volume was calculated using the formula for an ellipse (i.e. 4/3π·(l.w.h), where l, w, h are three radii of the tumor taken perpendicular to each other).

Treatment of mice with anti-PD-L1 or QH-II-066 occurred after 10 days tumor inoculation, as detailed in legends of relevant figures. α-PD-L1 antibody (200 μg; clone 10F9.G2) was in phosphate buffer saline (500 μL) and injected i.p. every third day per protocol, as antibody levels decrease and need to be maintained at a constant level. QH-II-066 was dissolved in 1% DMSO and 0.5% Tween-20 and injected i.p. at indicated doses daily for a week. Control mice in experiments were injected i.p. with vehicle for a week.

The invention claimed is:

1. A method of treating a $GABA_A$ receptor positive brain cancer comprising the steps of:

administering to a human subject diagnosed with a brain cancer radiation to the brain cancer and thereafter administering a therapeutically effective amount of 7-ethynyl-1-methyl-5-phenyl-1,3-dihydro-2H-benzo[e][1,4]diazepin-2-one or 7-ethynyl-5-(2-fluorophenyl)-1-methyl-1,3-dihydro-2H-benzo[e][1,4]diazepin-2-one or salt thereof and a therapeutically effective amount of an anti-checkpoint antibody to the human subject in need.

2. The method of claim 1 wherein the $GABA_A$ receptor positive brain cancer is a brain metastasis, or melanoma brain metastasis.

3. The method of claim 1, wherein the anti-checkpoint antibody is an anti-CTLA-4 antibody, anti-PD-1 antibody, anti-PD-L1 antibody, or combinations thereof.

4. The method of claim 1, wherein the anti-checkpoint antibody is ipilimumab, nivolumab, pembrolizumab, cemiplimab, atezolizumab, durvalumab, avelumab, or combinations thereof.

5. A method of treating $GABA_A$ receptor positive brain cancer comprising the steps of:

administering to a human subject diagnosed with a brain cancer radiation to the brain cancer and thereafter administering a therapeutically effective amount of 7-ethynyl-1-methyl-5-phenyl-1,3-dihydro-2H-benzo[e][1,4]diazepin-2-one or 7-ethynyl-5-(2-fluorophenyl)-1-methyl-1,3-dihydro-2H-benzo[e][1,4]diazepin-2-one or salt thereof and administering an effective amount of nivolumab and ipilimumab to the human subject in need.

6. The method of claim 5, wherein the $GABA_A$ receptor positive brain cancer is a brain metastasis, or melanoma brain metastasis.

* * * * *